US010232067B2

(12) United States Patent
Kim et al.

(10) Patent No.: US 10,232,067 B2
(45) Date of Patent: Mar. 19, 2019

(54) MOBILE DISINFECTOR USING UV LED

(71) Applicant: Seoul Viosys Co., Ltd., Ansan-si (KR)

(72) Inventors: Jong Rack Kim, Ansan-si (KR);
Chung Hoon Lee, Asan-si (KR); Dae Woong Suh, Ansan-si (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 460 days.

(21) Appl. No.: 14/478,967

(22) Filed: Sep. 5, 2014

(65) Prior Publication Data

US 2015/0064064 A1    Mar. 5, 2015

(30) Foreign Application Priority Data

Sep. 5, 2013   (KR) .......................... 10-2013-0106882

(51) Int. Cl.
*A61L 2/10*    (2006.01)
*F21L 4/02*    (2006.01)
*A61N 5/06*    (2006.01)

(52) U.S. Cl.
CPC ............. *A61L 2/10* (2013.01); *A61L 2202/15* (2013.01); *A61L 2202/16* (2013.01)

(58) Field of Classification Search
CPC ........................................................ A61L 2/10
USPC ........................................................ 422/24
See application file for complete search history.

(56) References Cited

U.S. PATENT DOCUMENTS

| | | | |
|---|---|---|---|
| 2005/0207159 A1* | 9/2005 | Maxik ........................ | F21K 9/00 362/254 |
| 2008/0231214 A1* | 9/2008 | Kim ........................ | A61N 5/0618 315/360 |
| 2011/0133654 A1* | 6/2011 | McKenzie ................ | F21K 9/00 315/152 |
| 2011/0243789 A1* | 10/2011 | Roberts ..................... | A61L 2/10 422/24 |
| 2013/0195716 A1 | 8/2013 | Fehr et al. | |
| 2014/0369038 A1* | 12/2014 | Tischler .................. | F21V 21/14 362/235 |

FOREIGN PATENT DOCUMENTS

KR      1020130085111 A      7/2013

* cited by examiner

*Primary Examiner* — Sean E Conley
*Assistant Examiner* — Holly M Mull
(74) *Attorney, Agent, or Firm* — Perkins Coie LLP

(57) ABSTRACT

A mobile disinfector using UV LEDs can include: a case forming an exterior structure of the disinfector; a cover including two parts coupled to respective sides of the case and including openings formed on the cover; and LED units exposed to outside through the openings formed on the cover. Since the cover is coupled to the case such that an angle between the cover and the case is adjusted, an irradiation angle of light emitted to the outside from the LED units is controlled.

8 Claims, 3 Drawing Sheets

MOBILE DISINFECTOR USING UV LED

CROSS-REFERENCES TO RELATED APPLICATIONS

This patent document claims priority to, and benefits of, a prior Korean application number 10-2013-0106882, filed on Sep. 5, 2013, which is incorporated by reference in its entirety.

BACKGROUND

The disclosure of this patent document relates to a disinfector including a mobile disinfector using ultraviolet (UV) light emitting diodes (LEDs).

Disinfection refers to an operation of eliminating viruses, bacteria, germs, or microorganisms. In general, disinfection may be divided into physical disinfection which heats and disinfects a target using heat or steam and chemical disinfection which disinfects a target using a disinfectant or sterilizing gas. Recently, recognition for health hazards in connection with viruses, bacteria, germs, or microorganisms or the like and the awareness or interest in good practices in maintaining health have increased among ordinary people. Thus, much attention has been paid to a device or method capable of easily performing disinfection.

SUMMARY

An embodiment of the present disclosure is directed to a mobile disinfector using UV LEDs, which includes UV LED units arranged on a movable cover so as to easily disinfect personal belongings.

Another embodiment of the present disclosure is directed to a mobile disinfector using UV LEDs, which includes LED units arranged on a movable cover to substantially prevent the occurrence of a blind spot onto which disinfecting UV light is not irradiated.

In one embodiment, a mobile disinfector using UV LEDs can include: a case forming an exterior structure of the disinfector; a cover having two parts coupled to respective sides of the case with openings formed on the cover; and multiple LED units disposed on the cover and exposed to outside through the openings formed on the cover. The cover is coupled to the case such that an angle between the cover and case is adjusted and an irradiation angle of light emitted to the outside from the LED units is controlled.

Various implementations of the disclosed embodiments may include one or more of the following features.

The case can be formed in a rectangular parallelepiped shape of which one side is longer than another side.

The LED units can provide UV light at a wavelength of 100 nm to 280 nm.

The cover can include a material formed on the front surface of the cover to increase a reflectance of UV light irradiated from the LED units. The material to increase the reflectance can include aluminum (Al).

The two parts of the cover can have a door-shaped structure which hinged to the respective sides of the case to open and close with respect to a front surface of the case.

The two parts of the cover can include: a left cover coupled to an edge of a left sidewall of the case to extend upward from the edge of the left sidewall when opened; and a right cover coupled to an edge of a right sidewall of the case to extend upward from the edge of the right sidewall when opened.

At least one of the left cover or the right cover can be coupled to the respective edges of the left or right sidewall to move up and down.

The LED units can be disposed on a rear surface of the cover, and have a light emitting surface exposed through the corresponding openings.

In another embodiment, a mobile disinfector using UV LEDs can include: a case forming an exterior structure of the disinfector and having a first group of openings formed on the case; a cover having two parts coupled to respective sides of the case and having a second group of openings formed on the cover; and LED units disposed on the cover exposed to outside through the second group of openings of the cover and LED units disposed on the case exposed to the outside through the first group of openings of the case. The cover is coupled to respective sides of the case to provide an adjustable angle between the cover and the case and control an irradiation angle of light emitted to the outside from the LED units disposed on the cover through the second group of openings.

In still another embodiment, a method of disinfecting an object is provided. In the method of disinfecting an object, a portable disinfector having a portable case and UV LEDs in the portable case to emit UV light for disinfecting the object is provided. A moveable cover coupled to the portable case is provided. The movable cover allows a user control of an angle of irradiation of the UV light emitted from UV LEDs disposed on the cover towards the object in a configuration in which the emitted UV light is transmitted through openings formed on the cover.

In accordance with the embodiments of the present disclosure, a user can carry the mobile disinfector using UV LEDs to disinfect a target.

Furthermore, the user can irradiate UV light to a desired part using the cover provided on the mobile disinfector. When the mobile disinfector is not used, the UV LEDs can be protected by the cover.

DESCRIPTION OF SPECIFIC EMBODIMENTS

Figure 1:
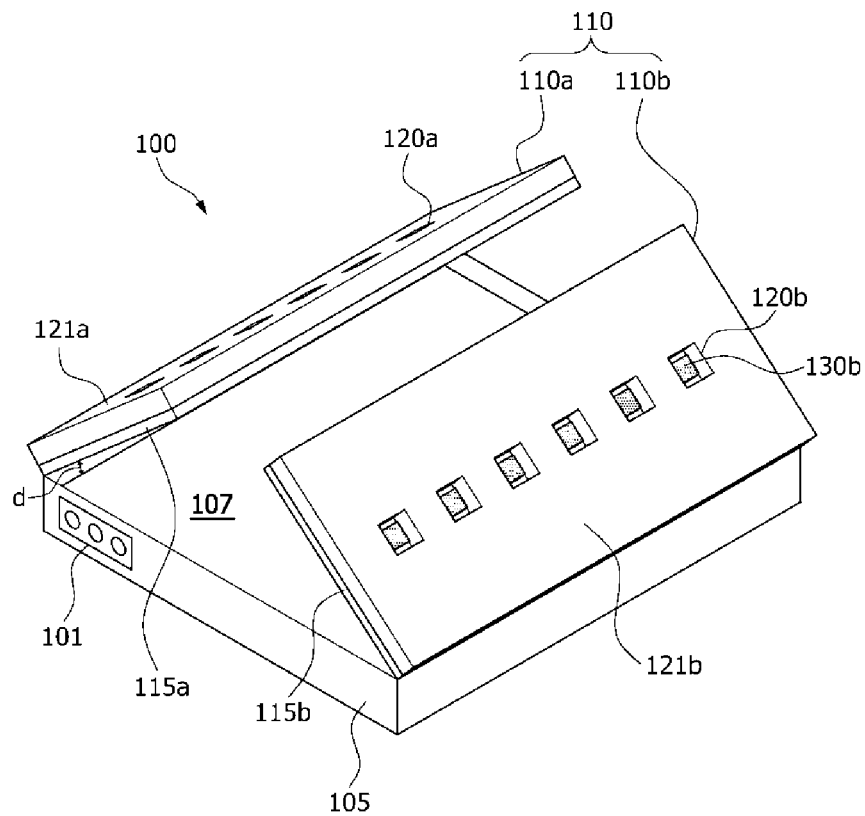
FIGS. 1 and 2 are diagrams illustrating an exemplary mobile disinfector using UV LEDs in accordance with an embodiment of the present disclosure.

Hereafter, embodiments of the present disclosure will be described in detail with reference to the accompanying drawings. It should be noted that the drawings are not to precise scale and may be exaggerated in some aspects, e.g., in thickness of lines or sizes of certain components, for descriptive convenience and clarity only. The drawings are illustrated from the point of view of an observer. When one element is referred to as being positioned over another element, it can indicate that the former element is directly positioned over the latter element or an additional element is intervened between the former element and the latter element.

In the drawings, like reference numerals denote substantially the same elements. Furthermore, the terms of a singular form can include plural forms unless referred to the contrary, and the term 'include', 'comprise', or 'have' specifies a property, a number, a step, a process, a part, or a combination thereof, and does not exclude other properties, numbers, steps, processes, parts, or combinations thereof.

The physical disinfection which is generally used to eliminate viruses, bacteria, germs, or microorganisms is to eliminate or substantially reduce microorganisms or the like by applying high-temperature heat or steam to a target. However, since various existing implementations of the physical disinfection tend to require time and fuel to achieve sufficiently high temperature conditions, it may take a long time to disinfect the target which may not be practical or desirable in various circumstances. In addition, since a user may be hurt by the high-temperature heat or steam due to various factors such as accidents, it is or can be difficult to manage the physical disinfection in practice. Furthermore, a disinfectant or sterilizing gas used in the chemical disinfection is generally a chemical material that exhibits some level of toxicity. Thus, a user can be exposed to a toxic material while the disinfectant or sterilizing gas is used.

Recently, with the increase in public awareness or recognition for germs or the like and interest in health among ordinary people, more and more people want to disinfect various personal belongings such as mobile phones. However, since most of disinfectors are large-sized, there are difficulties in using the disinfectors at homes.

Figure 2:
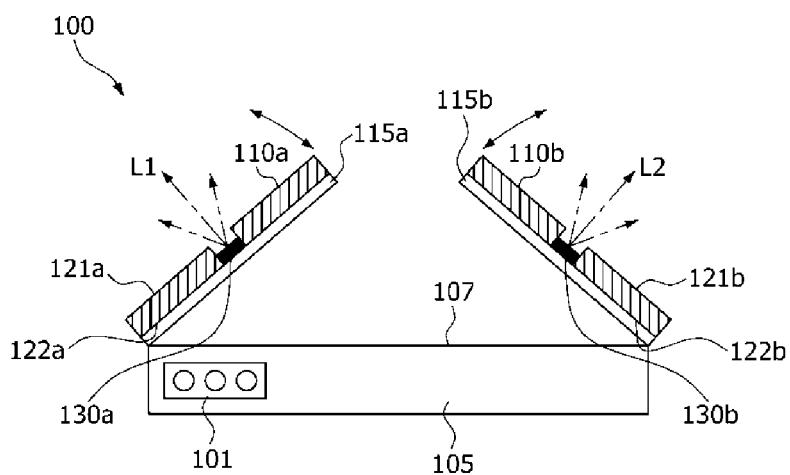

FIGS. 1 and 2 are diagrams illustrating an exemplary mobile disinfector using UV LEDs in accordance with an embodiment of the present disclosure. FIG. 2 is a diagram illustrating the operation of a cover of the mobile disinfector of FIG. 1.

Referring to FIGS. 1 and 2, the mobile disinfector 100 in accordance with an embodiment of the present disclosure can include a case 105, a cover 110, and LED units 130a and 130b, and a controller 101. The mobile disinfector 100 is sized and shaped to be portable to a site or object to be disinfected. The case 105 can form an exterior structure of the mobile disinfector 100. The cover 110 can include two separately moveable parts formed at respective sides of the case 105 and includes openings 120a and 120b. The LED units 130a and 130b can be disposed on the cover 110 and exposed to the outside through the openings 120a and 120b formed on the cover 110.

The case 105 forming the exterior structure of the mobile disinfector 100 can be formed in a rectangular parallelepiped shape of which one side is longer than another side. A front surface 107 of the case 105 can be formed in a flat plate shape or have a concave groove formed to a predetermined depth d.

In the specific example illustrated in FIGS. 1 and 2, the case 105 can include the two parts of the cover 110 extended upward from edges of respective side walls to adjust an angle between the two parts of the cover 110 and the respective side walls of the case 105 as the cover 110 is opened. The two parts of the cover 110 can include a left cover 110a and a right cover 110b, and have a door-shaped structure with the left cover 110a and the right cover 110b hinged at the edges of the respective side walls of the case 105. As indicated by bidirectional arrows of FIG. 2, the left cover 110a and the right cover 110b can be separately moved up and down so as to adjust an angle at which disinfection UV light is irradiated. Because the left cover 110a and the right cover 110b are coupled to the case 105 such that the angle thereof is adjusted with respect to the case 105, the irradiation angle of light emitted to the outside from the LED units 130a and 130b can be adjusted.

The left cover 110a and right cover 110b can include the openings 120a and 120b. For example, the left cover 110a can include the first openings, or a first group of openings, 120a formed on a front surface 121a of the left cover 110a, and the right cover 110b can include the second openings, or a second group of openings, 120b formed on a front surface 121b of the right cover 110b. The first or second group of openings 120a and 120b, or at least one of the first or second group of openings 120a and 120b, can be formed in a circular shape or a polygonal shape such as square or rectangle. The left cover 110a includes a first LED units or a first group of LED units 130a arranged on a rear surface 122a of the left cover 110a, and the right cover 110b includes a second LED units or a second group of LED units 130b arranged on a rear surface 122b of the right cover 110b. Each of the first and second LED units or first and second groups of LED units 130a or 130b can be installed as a module or package which includes LEDs disposed over a base member 115a or 115b with the LEDs emitting disinfecting UV light. The base member 115a or 115b can include a printed circuit board (PCB).

Referring to FIG. 2, the first or second LED units or at least one of first or second groups of LED units 130a or 130b can emit UV light in the UV-C region. Alternatively, the first or second LED units or at least one of first or second groups of LED units 130a or 130b can provide disinfecting UV light L1 or L2 at a wavelength of 200 nm to 400 nm or at a wavelength of 100 nm to 280 nm, in order to disinfect germs, bacteria, or microorganisms existing at or near the irradiation site. The first or second LED units or at least one of the first or second groups of LED units 130a or 130b has a light emitting surface exposed through the respective first or second openings or first or second group of openings 120a or 120b. The first or second LED units or at least one of the first or second groups of LED units 130a or 130b can be arranged in a line. In another embodiment, the first or second LED units or at least one of the first or second groups of LED units 130a or 130b can be arranged in two lines with UV LED chips arranged in parallel to each other with a predetermined distance between the two parallel lines.

If LED units for providing disinfecting UV light are arranged on the front surface 107 of the case 105, the LED units would be fixed only on one surface. Thus, the region onto which disinfecting UV light is irradiated can be limited, and a blind spot onto which disinfection UV light is not irradiated can occur. Furthermore, it is difficult to irradiate disinfecting UV light in a lateral direction.

In the mobile disinfector in accordance with an embodiment of the present disclosure, the LED units (e.g., LED units 130a and 130b) can be arranged on the left cover 110a and the right cover 110b, and the left cover 110a and the right cover 110b can be separately moved up and down to prevent, or substantially prevent, the occurrence of a blind spot onto which disinfecting UV light is not irradiated. Furthermore, as indicated by the bidirectional arrows of FIG. 2, the left cover 110a and the right cover 110b can be separately moved up and down so as to adjust the angle at which disinfecting UV light is irradiated.

For example, when the first group of LED units 130a arranged on the left cover 110a irradiates disinfecting UV light L1 in a first direction, the second group of LED units 130b arranged on the right cover 110b can irradiate disinfecting UV light L2 in a second direction different from the first direction. Thus, it is possible to prevent, or substantially avoid, a blind spot onto which disinfecting UV light is not irradiated. In this case, at least one of the front surface 121a of the left cover 110a or the front surface 121b of the right cover 110b can be formed of a material having a high reflectance, such as aluminum (Al), in order to increase the irradiation amount of UV light provided from at least one of the first or second group of LED units 130a or 130b.

The controller 101 can be arranged on an outer surface of the case 105. Although not illustrated in the drawing, the controller 101 can include a power on-off button and a timer for controlling the operation time of at least one of the first or second group of LED units 130a or 130b. When a time duration for disinfection passes, the timer can automatically shut off power applied to at least one of the first or second group of LED units 130a or 130b to increase a lifetime of the groups of LED units.

Figure 3:
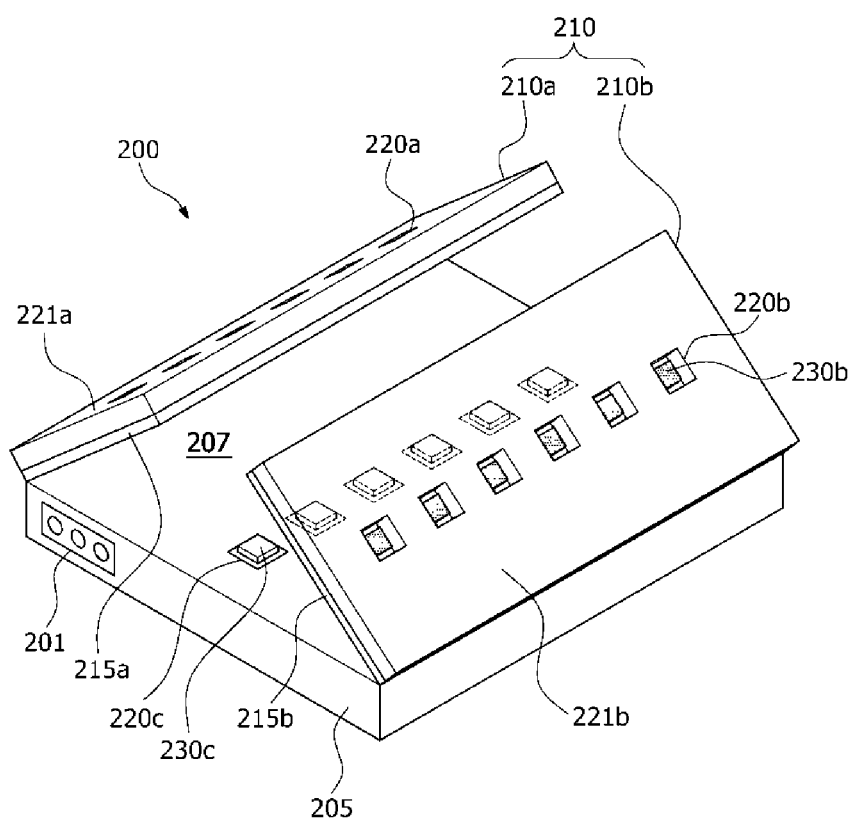
FIGS. 3 to 5 are diagrams illustrating an exemplary mobile disinfector using UV LEDs in accordance with another embodiment of the present disclosure.
Figure 4:
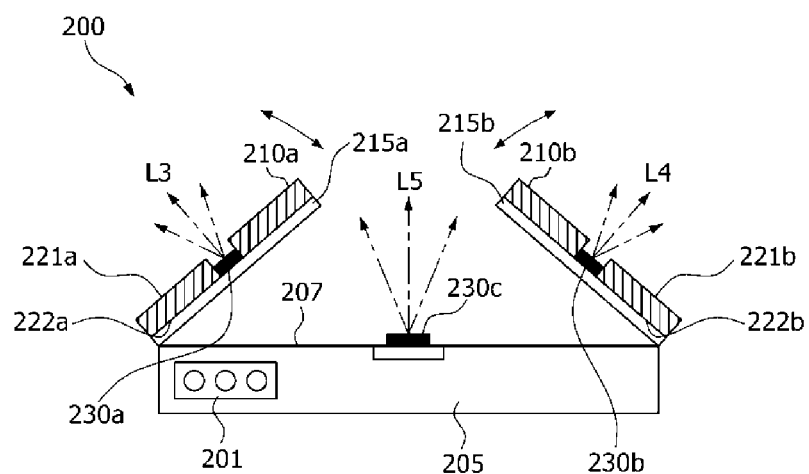
Figure 5:
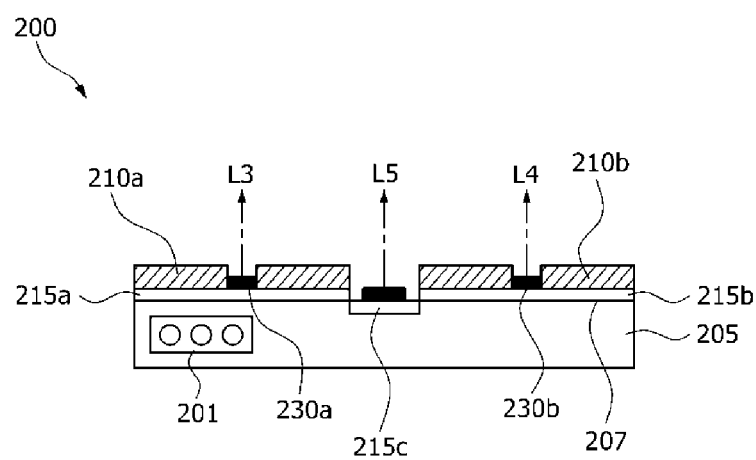

FIGS. 3 to 5 are diagrams illustrating an exemplary mobile disinfector using UV LEDs in accordance with another embodiment of the present disclosure. FIG. 4 is a diagram for explaining an exemplary operation of a cover of the mobile disinfector of FIG. 3. FIG. 5 illustrates an exemplary state in which the cover of FIG. 3 is closed.

Referring to FIGS. 3 and 4, a mobile disinfector 200 in accordance with the other embodiment of the present disclosure can include a case 205, a cover 210, first and second groups of LED units 230a and 230b disposed on the cover 210, third LED units or a third group of LED units 230c disposed on the case 205, and a controller 201. The mobile disinfector 200 is sized and shaped to be portable to a site or object to be disinfected. The cover 210 can include a left cover 210a and a right cover 210b formed at respective sides of the case 205 and includes openings 220a and 220b respectively. The first and second LED units 230a and 230b can be disposed on the cover 210 and exposed to the outside through first and second groups of openings 220a and 220b formed on the cover 110. The case 205 forms an exterior structure of the mobile disinfector 200, and includes third openings or a third group of openings 220c formed on the case 205. The third LED units or third group of LED units 230c are arranged on a front surface 207 of the case 205, and exposed to the outside through the third openings or third group of openings 220c. The left cover 210a and the right cover 210b are formed to be hinged at respective sides of the case 205 and includes the first and second openings or first and second groups of openings 220a and 220b, respectively. The first and second LED units or first and second groups of LED units 230a and 230b are exposed to the outside through the first and second openings or first and second groups of openings 220a and 220b formed on the cover 210.

The case 205 forming the exterior structure of the mobile disinfector 200 can be formed in a rectangular parallelepiped shape of which one side is longer than another side. The front surface 207 of the case 205 can be formed in a flat plate shape.

The case 205 can include the left cover 210a and right cover 210b extended upward from edges of respective side walls and hinged to have an adjustable angle between the left and right covers 210a and 210b and the case 205. The cover 210 can include the left cover 210a and the right cover 210b having a door-shaped structure hinged to edges of respective side walls of the case 205 to have an adjustable angle when opened and closed. As indicated by bidirectional arrows of FIG. 4, at least one of the left cover 210a or the right cover 210b can be separately moved up and down so as to adjust the angle at which disinfecting UV light is irradiated. The left cover 210a and right cover 210b can include the first and second openings or first and second groups of openings 220a and 220b respectively. For example, the left cover 210a can have the first openings or first group of openings 220a formed on a front surface 221a of the left cover 210a, and the right cover 210b can have the second openings or second group of openings 220b formed on a front surface 221b of the right cover 210b. The first or second openings or at least one of the first or second groups of openings 220a and 220b can be formed in a circular shape or polygonal shape such as square or rectangle. The first LED units or first group of LED units 230a can be arranged on a rear surface 222a of the left cover 210a, and the second LED units or second group of LED units 230b can be arranged on a rear surface 222b of the right cover 210b. The first or second LED units or at least one of first or second group of LED units 230a or 230b can be installed as a module or package which includes LEDs disposed over a base member 215a or 215b with the LEDs emitting disinfecting UV light. The base member or at least one of the base members 215a or 215b can include a PCB.

The third LED units or third group of LED units 230c are formed on the front surface 207 of the case 205, and exposed through the third openings or third group of openings 220c. The third LED units or third group of LED units 230c can emit UV light in the UV-C range. Alternatively, the third LED units or third group of LED units 230a can provide disinfecting UV light at a wavelength of 200 nm to 400 nm or at a wavelength of 100 nm to 280 nm, and disinfect germs, bacteria, or microorganisms existing at or near the irradiation site. The third LED units 230c can be arranged in a line.

Referring to FIG. 4, the first or second LED units or at least one of first or second LED units 230a or 230b can emit disinfecting UV light at the same wavelength as the third LED units 230c. For example, the first or second LED units or at least one of first or second group of LED units 230a or 230b can provide UV light L3 or L4 in the UV-C range. The first or second LED units or at least one of first or second groups of LED units 230a or 230b can have a light emitting surface exposed to the outside through the first or second openings or first or second group of openings 220a or 220b. The first or second LED units or at least one of first or second LED units 230a or 230b can be arranged in a line.

In the mobile disinfector 200 in accordance with the other embodiment of the present disclosure, the LED units (e.g., first and second LED units or first and second groups of LED units 230a and 230b) can be arranged on the left cover 210a and the right cover 210b respectively. The left cover 210a or the right cover 210b or both left and right covers 210a and 210b can be separately moved up and down to prevent the occurrence of a blind spot onto which disinfecting UV light is not irradiated. Because the covers 110a and 110b are coupled and hinged to the case 205 such that an angle between individual covers 110a and 110b and the case 205 is adjusted, an irradiation angle of light emitted to the outside from the first or second LED units or first or second groups of 230a or 230b through the first or second openings or first or second groups of openings 220a or 220b can be controlled.

For example, the first group of LED units 230a arranged on the left cover 210a can irradiate disinfecting UV light L3 in a first lateral direction, and the second group of LED units 230b arranged on the right cover 210b can irradiate disinfecting UV light L4 in a second lateral direction different from the first lateral direction. Furthermore, because disinfection is also performed in a forward direction by disinfecting UV light L5 irradiated from the third LED units or third group of LED units 230c on the front surface 207 of the case 205, the disinfection efficiency can be improved in the forward direction as well as the lateral direction. As indicated by bidirectional arrows of FIG. 4, the left cover 210a or the light cover 210b or both left and right covers 210a and 210b can be separately moved up and down so as to adjust the angle at which disinfecting UV light is irradiated in the lateral direction. The front surface 221a or front surface 221b or both surfaces 221a and 221b of the left cover 210a or the right cover 210b can be formed of a material having a high reflectance, such as Al, in order to increase the irradiation amount of UV light provided from the first or second LED units or at least one of the first or second groups of LED units 230a or 230b.

When a user wants to intensively disinfect a surface of a target object, the user can increase the intensity of the disinfecting UV light. Increasing the intensity of the disinfecting UV light can improve the disinfection efficiency while reducing the disinfection time. As illustrated in FIG. 5, when the left cover 210a and the right cover 210b are fixed on the front surface 207 of the case 205, the disinfection UV lights L3, L4, and L5 irradiated from the first LED units or first group of LED units 230a, the second LED units or second group of LED units 230b, and the third LED units or third group of LED units 230c can be provided in the same direction, for example, in the forward direction. Because the disinfecting UV lights L3, L4, and L5 can be focused together in a specific direction, the intensity of the disinfecting UV light in total can be increased to improve the disinfection efficiency.

The controller 201 can be arranged on an outer surface of the case 205. The controller 201 can include a power on-off button and a timer for controlling an operation time of the first, second, or third LED units or at least one of first, second or third group of LED units 230a, 230b or 230c. When the time duration for disinfection passes, the timer can automatically shut off power applied to at least one of the first, second, or third LED units 230a, 230b or 230c to increase a lifetime of the LED units.

In the disinfector in accordance with the embodiments of the present disclosure, the LED units can be moved up and down because the LED units are arranged on the cover having a door-shaped structure with an adjustable angle. Thus, the disinfector can irradiate disinfecting UV light in the lateral direction as well as the forward direction to prevent or substantially prevent the occurrence of a blind spot onto which disinfecting UV light is not irradiated. Furthermore, since the disinfection UV light is induced to be focused in a specific direction, the intensity of the disinfection UV light can be increased to improve the disinfection efficiency.

Only a few embodiments, implementations and examples are described and other embodiments and implementations, and various enhancements and variations can be made based on what is described and illustrated in this document.

What is claimed is:

1. A mobile disinfector using ultraviolet (UV) light emitting diodes (LEDs), comprising:

a case forming an exterior structure of the disinfector and having a first group of openings formed on the case, the case having a first width;

a cover including two parts coupled to respective sides of the case and having a second group of openings formed on the cover, each of the two parts having a second width that is smaller than a half of the first width; and LED units disposed on the two parts of the cover exposed to outside through the second group of openings of the cover and LED units disposed on the case exposed to the outside through the first group of openings of the case, wherein the cover is coupled to respective sides of the case to provide an adjustable angle between the cover, and when the angle is adjusted so that the cover is disposed on a surface of the case, the LED units disposed on the case are not covered by the two parts and the LED units disposed on the case and the LED units on the two parts of the cover provide UV light in a same direction away from the case.

2. The mobile disinfector of claim 1, wherein at least one of the LED units disposed on the cover or the case provide UV light at a wavelength of 100 nm to 280 nm.

3. The mobile disinfector of claim 1, wherein the two parts of the cover have a door-shaped structure hinged to the respective sidewalls of the case to open and close with respect to a front surface of the case.

4. The mobile disinfector of claim 1, wherein the two parts of the cover comprises:

a left cover coupled to an edge of a left sidewall of the case to extend upward from the edge of the left sidewall when opened; and a right cover coupled to an edge of a right sidewall of the case to extend upward from the edge of the right sidewall when opened.

5. The mobile disinfector of claim 4, wherein at least one of the left cover or the right cover is coupled to the respective edges of the left or right sidewalls to move up and down.

6. The mobile disinfector of claim 4, wherein the left cover and the right cover are fixed to a front surface of the case such that the LED units disposed on the cover and exposed through the first and second group of openings are fixed in a same horizontal direction.

7. The mobile disinfector of claim 1, wherein the LED units disposed on the case are disposed on a front surface of the case.

8. The mobile disinfector of claim 7, wherein the same direction is from the first surface to be further away from the second surface.

* * * * *